(12) United States Patent
Nielsen et al.

(10) Patent No.: US 9,511,244 B2
(45) Date of Patent: Dec. 6, 2016

(54) RETROSPECTIVE CALCULATION OF RADIATION DOSE AND IMPROVED THERAPY PLANNING

(71) Applicant: KONINKLIJKE PHILIPS N.V., Eindhoven (NL)

(72) Inventors: Tim Nielsen, Eindhoven (NL); Peter Boernert, Eindhoven (NL); Falk Uhlemann, Eindhoven (NL); Johannes Adrianus Overweg, Eindhvoen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/881,472

(22) Filed: Oct. 13, 2015

(65) Prior Publication Data
US 2016/0030770 A1 Feb. 4, 2016

Related U.S. Application Data

(62) Division of application No. 13/496,208, filed as application No. PCT/IB2010/054189 on Sep. 16, 2010, now Pat. No. 9,188,654.

(Continued)

(51) Int. Cl.
*A61B 6/00* (2006.01)
*A61N 5/10* (2006.01)
(Continued)

(52) U.S. Cl.
CPC .......... *A61N 5/1071* (2013.01); *A61N 5/1031* (2013.01); *A61N 5/1039* (2013.01); *A61N 5/1049* (2013.01);
(Continued)

(58) Field of Classification Search
CPC .... A61N 5/1049; A61N 5/103; A61N 5/1042; A61N 5/1065; A61N 5/1031
See application file for complete search history.

(56) References Cited

U.S. PATENT DOCUMENTS

| 6,806,712 | B2 * | 10/2004 | Akgun | ............... A61B 5/055 324/309 |
| 7,574,251 | B2 * | 8/2009 | Lu | ........................ A61N 5/103 600/411 |

(Continued)

FOREIGN PATENT DOCUMENTS

| JP | 2009160307 A | 7/2009 |
| WO | 2005031629 A2 | 4/2005 |
| WO | 2006039009 A2 | 4/2006 |

OTHER PUBLICATIONS

Raaymakers, B.W. et al Integrating a 1.5 T MRI Scanner with a 6 MV accelerator: proof of concept 2009; Phys. Med. Biol. 54 N229-N237.

*Primary Examiner* — Baisakhi Roy

(57) ABSTRACT

A combined magnetic resonance (MR) and radiation therapy system includes a bore-type magnet with a magnet radiation translucent region which allows radiation beams to travel radially through the magnet and a split-type gradient coil includes a gradient coil radiation translucent region aligned to the magnet radiation translucent region. A radiation source, disposed laterally to the magnet, administers a radiation dose through the magnet and gradient coil radiation translucent regions to an examination region. A dosage unit determines the actual radiation dose delivered to each voxel of a target volume and at least one non-target volume based on a pre-treatment, intra-treatment, and/or post-treatment image representation of the target volume and the at least one non-target volume. A planning processor updates at (Continued)

least one remaining radiation dose of a radiation therapy plan based on the determined actual radiation dose.

15 Claims, 6 Drawing Sheets

Related U.S. Application Data

(60) Provisional application No. 61/248,975, filed on Oct. 6, 2009.

(51) Int. Cl.
  *G01R 33/381* (2006.01)
  *G01R 33/48* (2006.01)
  *G01R 33/38* (2006.01)
  *G01R 33/56* (2006.01)

(52) U.S. Cl.
  CPC ......... *G01R 33/381* (2013.01); *G01R 33/4808* (2013.01); *A61N 2005/1055* (2013.01); *A61N 2005/1058* (2013.01); *G01R 33/3806* (2013.01); *G01R 33/5601* (2013.01)

(56) References Cited

U.S. PATENT DOCUMENTS

| | | | |
|---|---|---|---|
| 2004/0024434 A1* | 2/2004 | Yang | A61B 18/1492 607/96 |
| 2005/0111621 A1* | 5/2005 | Riker | A61N 5/1031 378/65 |
| 2006/0285639 A1 | 12/2006 | Olivera et al. | |
| 2007/0041497 A1* | 2/2007 | Schnarr | A61N 5/103 378/65 |
| 2007/0049785 A1 | 3/2007 | Pekar et al. | |
| 2008/0002811 A1 | 1/2008 | Allison | |
| 2008/0208034 A1 | 8/2008 | Yang et al. | |
| 2008/0208036 A1 | 8/2008 | Amies et al. | |
| 2009/0028408 A1 | 1/2009 | Spies et al. | |
| 2009/0175418 A1 | 7/2009 | Sakurai | |
| 2010/0292564 A1* | 11/2010 | Cantillon Murphy | G01R 33/4804 600/411 |

* cited by examiner

RETROSPECTIVE CALCULATION OF RADIATION DOSE AND IMPROVED THERAPY PLANNING

This application is a divisional of U.S. patent application Ser. No. 13/496,208, filed Mar. 15, 2012, which is a National Stage filing under 35 U.S.C. §371(c) of International Application No. PCT/IB2010/054189, filed Sep. 16, 2010, which claims priority to U.S. Provisional Application 61/248,975 filed Oct. 6, 2009, the disclosures of which are incorporated by reference in their entirety.

DESCRIPTION

The present application relates to a method and system for improved planning and delivery of radiation therapy. It finds particular application to combined magnetic resonance imaging (MRI) and radiotherapy systems capable of simultaneous MR imaging and irradiation, but it may find application in other imaging or spectroscopy modalities or other types of treatment.

Radiation therapy is a common therapeutic technique in oncology in which a dose of high energy gamma (Γ) radiation, particle beam, or other radiation is delivered to a patient's body to achieve a therapeutic effect, i.e. eradicate cancerous tissue. The dose is fractionated, or spread out over a period of several weeks, for several reasons. Since the radiation beam travels through healthy tissue on its way to the target, fractionation allows for the healthy tissue damaged during treatments to recover, without allowing the less efficient cancer tissue to repair between fractions.

To minimize unwanted damage while maintaining a therapeutic effect, a therapy plan is generated prior to treatment which details the fractionation schedule along with optimal beam shape and direction. Typically a static volumetric image, e.g. a computed tomography (CT) image, of the tumor and surrounding tissue is acquired. A computerized planning system automatically or semi-automatically delineates contours of the target volume, healthy surrounding tissue, and sensitive areas at risk of being damaged, such as the spinal cord, glands, or the like, radiation blocking or attenuating tissue, such as bone, etc. Using the contour data, the planning system then determines an optimal treatment plan which details the radiation dose distribution and fractionation schedule along with radiation beam direction and shape.

Prior to a radiation treatment, an image, e.g. fluoroscopic, x-ray, or the like, of the target volume is taken to align the target volumes position to the radiation therapy coordinate system and to verify the accuracy of the current therapy plan. The therapy plan can lose accuracy during the treatment process because of positioning accuracy, day-to-day variations in organ position, breathing, heartbeat, increases/decreases in tumor size, and other physiological processes, e.g. bladder filling or the like. To account for such uncertainties and achieve the intended therapeutic effect, current methods involve irradiating a volume slightly larger than the target volume determined from the static volumetric image. This approach leads to increased damage to healthy tissue and can lead to extraneous side effects. If the current therapy plan significantly changes, e.g. if the target volume size has shrunk due to treatment, it can be cancelled and a new therapy plan is generated which can be time-consuming.

The present application provides a new and improved MRI based image guided radiotherapy dose planning which overcomes the above-referenced problems and others.

In accordance with one aspect, a method for radiation dose delivery includes generating a radiation therapy plan, the radiation therapy plan includes a plurality of radiation doses. A pre-treatment image representation of a target volume and non-target volumes is acquired and a contour and position of the target volume and at least one non-target volume is determined based on the pre-treatment image representation. A radiation dose including a plurality of radiation beam trajectories and at least one radiation beam geometry is administered. An actual radiation dose delivered to each region of the target volume and the at least one non-target volume is determined based on their determined contours and positions, the radiation beam trajectories and the at least one radiation beam geometry.

In accordance with another aspect, a magnetic resonance guided radiotherapy device includes a bore-type magnet which generates a static magnetic field in an examination region, the magnet being configured with a magnet radiation translucent region which allows radiation beams to travel radially through the bore-type magnet into a subject disposed therein. A split-type gradient coil which defines a gap including a gradient coil radiation translucent region aligned to the magnet radiation translucent region, the split-type coil being configured to apply selected magnetic field gradient pulses across the imaging region. A radiofrequency (RF) coil is configured to induce and manipulate magnetic resonance in a subject in the examination region and/or acquire magnetic resonance data from the examination region. A radiation source disposed laterally to the bore-type magnet, the radiation source being positioned to transmit the radiation beams through the magnet and gradient coil radiation translucent regions to an isocenter of the bore-type magnet and a scanner controller which controls the gradient coil and RF coil to generate an image representation.

One advantage relies in that radiation exposure to healthy tissue is reduced.

Still further advantages of the present invention will be appreciated by those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
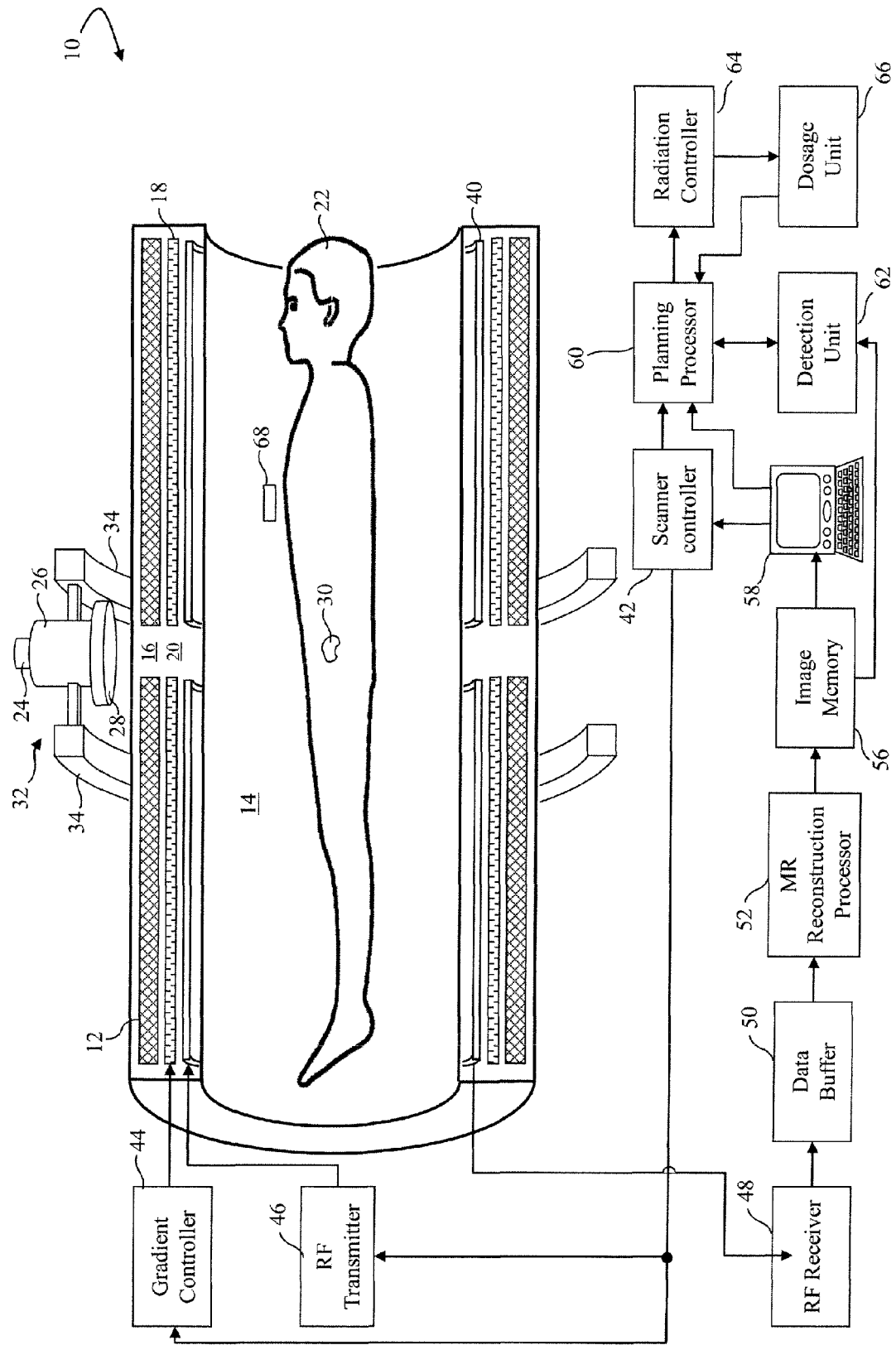
FIG. 1 is a diagrammatic illustration of a combined magnetic resonance (MR) and radiotherapy system.

With reference to FIG. 1, a combined magnetic resonance (MR) and radiotherapy system 10 includes a main magnet 12 which generates a temporally uniform $B_0$ field through an examination region 14. The main magnet can be an annular or bore-type magnet, a C-shaped open magnet, other designs of open magnets, or the like. The magnet includes a magnet radiation translucent region 16 which allows a radiation beam, such as gamma (Γ) rays, x-rays, particle beams, or the like, to pass through the magnet. In one embodiment, the main magnet 12 is a bore-type magnet. The magnet radiation translucent region 16 is arranged circumferentially to allow the radiation beam to travel radially through an isocenter of the bore. Gradient magnetic field coils 18 disposed adjacent the main magnet serve to generate magnetic field gradients along selected axes relative to the $B_0$ magnetic field for spatially encoding magnetic resonance signals, for producing magnetization-spoiling field gradients, or the like. The gradient magnetic field coils 18 include a gradient radiation translucent region 20 aligned to the magnet radiation translucent region 16 to allow the radiation beam to travel through the main magnet 12 and gradient magnetic field coils 18 in a predictable manner to a subject 22 in the examination region 14, i.e. the absorption throughout the radiation translucent regions 16, 20 is constant. The magnetic field gradient coil 18 may include coil segments configured to produce magnetic field gradients in three orthogonal directions, typically longitudinal or z, transverse or x, and vertical or y directions.

The radiation beam originates from a radiation source 24, such as a linear accelerator or the like, disposed laterally to the main magnet 12 and adjacent to the radiation translucent regions 16, 20. An absorber 26 absorbs any radiation from the source 24 travelling in an unwanted direction. A collimator 28 helps shaping the beam of radiation to localize the treatment to a target volume 30. In one embodiment, the collimator is an adjustable collimator, such as a multi-leaf collimator (MLC) or the like, which modulates the radiation beam geometry. The leaves of the MLC allow for conformal shaping of the radiation beam to match the shape of the target volume 30 from each angular position of the radiation beam around the subject.

A radiation source assembly 32, composed of the radiation source 24, the absorber 26, and the collimator 28, is mounted on a rail system 34 which allows the radiation source assembly to be rotated circumferentially about the radiation translucent regions 16, 20 to a plurality of positions permitting a corresponding number of radiation beam trajectories. Alternatively, the radiation source assembly can move continuously with its cross section and intensity also modulated on a continuum. It should be appreciated that other positioning systems or methods are also contemplated, for example a fixed rail system, a non-fixed rail system, a single rail system, multi-rail system, C-arm, or the like. In one embodiment, the radiation source assembly is rotatable 360° about the bore-type magnet 12; however, in clinical practice it is not necessary for such a wide range. In another embodiment, a plurality of radiation source assemblies are positioned circumferentially about the radiation translucent regions 16, 20, each radiation source assembly having a substantially fixed trajectory. This arrangement allows for a reduced radiation therapy session duration which may be advantageous to larger or anxious subjects. It should be noted that, the radiation source assembly and rail system can be constructed from non-ferromagnetic materials so as not to interfere or be interfered with the main magnet or gradient magnetic field coils.

A radio-frequency (RF) coil assembly 40, such as a whole-body radio frequency coil, is disposed adjacent to the examination region. The RF coil assembly generates radio frequency pulses for exciting magnetic resonance in aligned dipoles of the subject. The radio frequency coil assembly 40 also serves to detect magnetic resonance signals emanating from the imaging region. The whole body coil can be of a single coil or a plurality of coil elements as part of an array. The RF coil assembly is configured such that it does not obscure or is radiation translucent adjacent to the radiation translucent regions 16, 20.

To acquire magnetic resonance data of a subject, the subject is placed inside the examination region 14, preferably at or near an isocenter of the main magnetic field. A scan controller 42 controls a gradient controller 44 which causes the gradient coils to apply the selected magnetic field gradient pulses across the imaging region, as may be appropriate to a selected magnetic resonance imaging or spectroscopy sequence. The scan controller 42 also controls at least one RF transmitter 46 which causes the RF coil assembly to generate magnetic resonance excitation and manipulation of $B_1$ pulses. The scan controller also controls an RF receiver 48 which is connected to the whole-body or local RF coils to receive magnetic resonance signals therefrom.

The received data from the receiver 48 is temporarily stored in a data buffer 50 and processed by a magnetic resonance data processor 52. The magnetic resonance data processor can perform various functions as are known in the art, including image reconstruction, magnetic resonance spectroscopy, and the like. Reconstructed magnetic resonance images, spectroscopy readouts, and other processed MR data are stored in an image memory 56 and displayed on a graphic user interface 58. The graphic user interface 58 also includes a user input device which a clinician can use for controlling the scan controller 42 to select scanning sequences and protocols, and the like.

Prior to receiving radiotherapy, a planning processor 60, automatically or by user guidance, generates a fractionated radiation therapy plan; each therapy plan includes a plurality of fractions or radiation doses. Each radiation dose includes a prescribed radiation dose, a plurality of radiation beam trajectories, and at least one radiation beam geometry (cross section). The amount of radiation used in radiotherapy is measured in grays (Gy), and varies depending on the type, size, and stage of the tumor being treated. For example, a radiation therapy plan which mandates a radiation dose of 60 Gy can be fractionated into 30 radiation dosage plans of 2 Gy, wherein each radiation dosage plan is administered five days a week for a total of six weeks. In each session, the radiation is distributed over a plurality of trajectories, e.g. 20, along which the same or varying portions of the session dose is delivered. Typically, radiation dosage plan for an adult is 1.8-2.0 Gy and 1.5-1.8 Gy for a child.

To determine the radiation beam trajectories and geometry, a detection unit 62 detects the target volume 30 and non-target volumes, which will be described in detail later, by determining their contours from high-resolution 3D images by using image processing techniques and/or models that describe to volumes. Image processing techniques may include any combination of automatic or semi-automatic segmentation, edge detection, principal components analysis, or the like and can be combined with a model that describes the volumes' shape, texture, motion, or the like to further enhance detection. The determined contours are stored in memory within the detection unit 62 itself for later use. In one embodiment, the high resolution 3D image representation is an MR image representation acquired from the combined MR and radiotherapy system 10 and is retrieved from the image memory 56 for contour delineation. Alternatively, the high resolution 3D image representation can be acquired using other imaging modalities, e.g. computed tomography (CT), x-ray, x-ray fluoroscopy, ultrasound, or the like.

The planning processor 60 uses the determined contours to generate the individual radiation doses and stores them in memory within the processor itself. Certain non-target volumes, such as radiation blocking or attenuating tissue and sensitive tissue like tissue, organs, glands, or the like, should avoid receiving radiation. The planning processor determines beam trajectories which maximize radiation exposure to target volume while sparing non-target volumes from unwanted damage. Unfortunately, the position and shape of these volumes can fluctuate on a daily basis due to a number of physiological changes such as breathing, bladder volume, lung inflation/deflation, weight gain/loss, tumor size, daily variations in organ position, or the like. Instead of over compensating by irradiating a slightly larger area or generating a new radiation therapy plan altogether, the current radiation therapy plan can be updated by determining the dose delivered to each part of the target and non-target volumes after each treatment. A subsequent radiation dose, or all of the subsequent doses, can be altered based on the delivered radiation dose.

Figure 2:
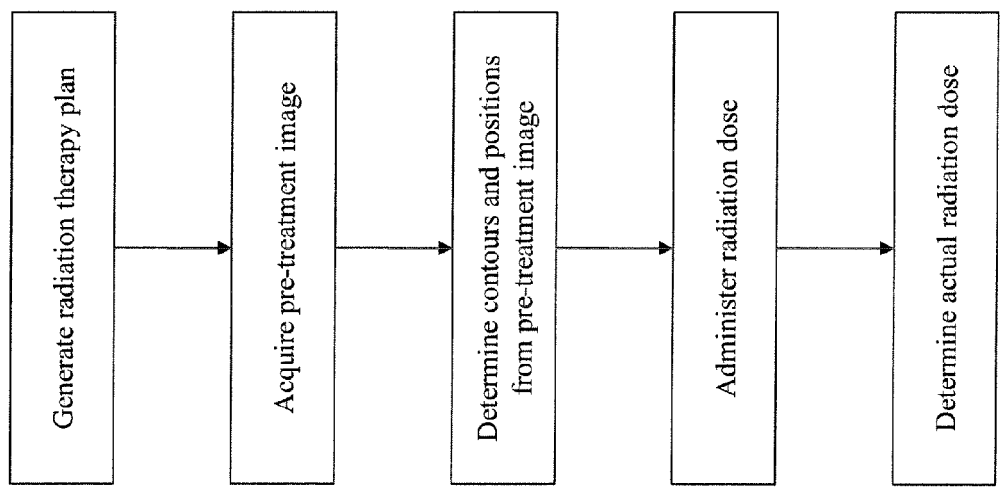
FIG. 2 is a flow chart of a method for radiation treatment.

With reference to FIG. 2, in one aspect, after the radiation dose is delivered, the actual dose delivered to each voxel of the target 30 and non-target volumes is determined based on a pre-treatment image. Prior to administration of a radiation dose, the scanner controller 42 controls the MR system to acquire a 3D pre-treatment image representation of the target volume 30 and non-target volumes. The pre-treatment image can be a low-resolution 3D image representation from which the detection unit 62 determines the contours and positions of the target volume 30 and the non-target volumes. The planning processor 60 aligns the current target volume 30 position to the coordinate system of the radiation source assembly 32. Optionally, surgically implanted markers and/or landmarks can be used to ease alignment. A radiation controller 64 controls the radiation source assembly 32, i.e. its rotational position, the leaves of the MLC 28, and the radiation source 24, to administer treatment at the beam trajectories and geometry according to the current radiation dose. After treatment, a dosage unit 66 uses the current beam trajectories, current beam geometry, and the determined contours and/or positions from the pre-treatment image representation to determine the actual radiation dose delivered to each voxel of the target volume 30 and non-target volumes. The planning processor 60 updates the remaining radiation therapy plan, i.e. at least one or all of the subsequent radiation doses, according to the actual radiation delivered to the target volume 30 and non-target volumes.

Figure 3:
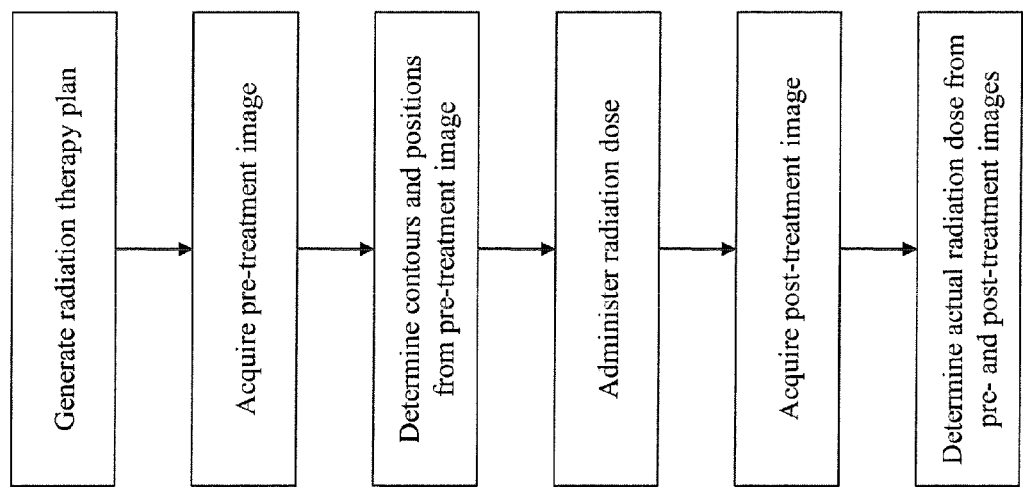
FIG. 3 is a flow chart of another method for radiation dose delivery.

With reference to FIG. 3, in a second aspect, after the radiation dose is delivered, the actual dose delivered to each voxel of the target 30 and non-target volumes is determined based on a pre-treatment image and a post-treatment image. After the administration of a radiation dose, the scanner controller 42 controls the MR system to acquire a post-treatment image representation of the target volume 30 and non-target volumes. The detection unit 62 determines the contours and positions of the target volume 30 and the non-target volumes. The dosage unit 66 determines the actual radiation dose delivered to each voxel of the target volume 30 and non-target volumes based on the current beam trajectories, current beam geometry, and changes of the determined contours and/or positions between the pre-treatment and post-treatment image representations. By comparing the position of the target 30 and non-target volumes in the pre-treatment and post-treatment image representations, the accuracy of the determined actual dose can be improved. The planning processor 60 updates the remaining radiation therapy plan, i.e. at least one or all of the subsequent radiation doses, according to the actual radiation delivered to the target volume 30 and non-target volumes.

Figure 4:
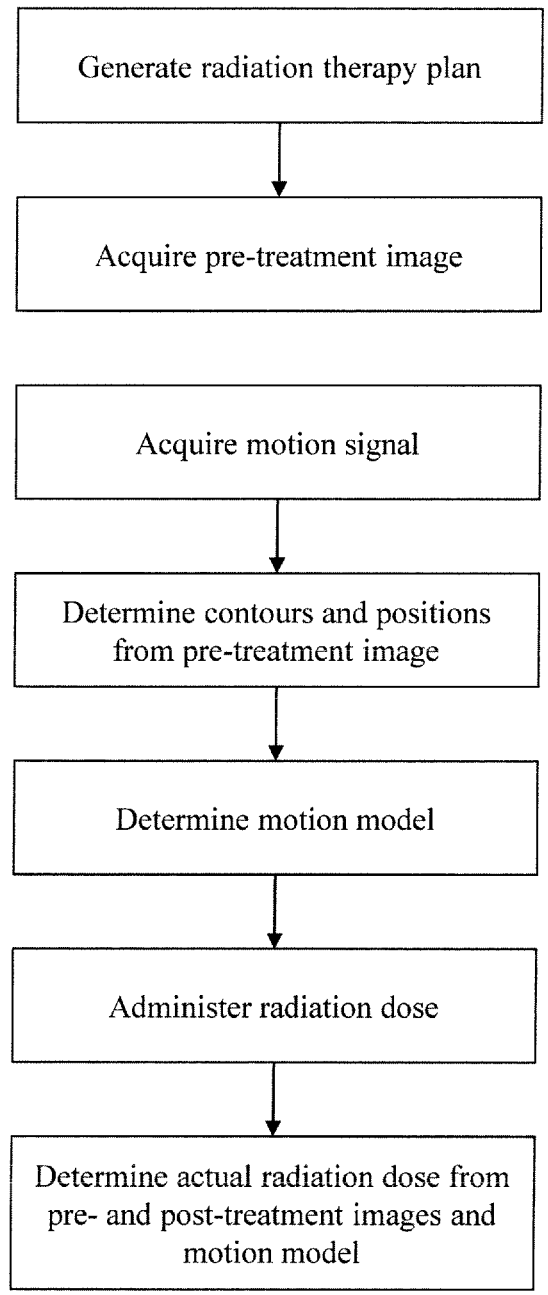
FIG. 4 is a flow chart of another method for radiation dose delivery.

With reference to FIG. 4, in a third aspect, after the radiation dose is delivered, the actual dose delivered to each voxel of the target 30 and non-target volumes is determined based on a pre-treatment image and a motion model. Prior to administration of a radiation dose, the scanner controller 42 controls the MR system to acquire a 3D pre-treatment image representation of the target volume 30 and non-target volumes and acquire a motion signal from an external sensor 68, e.g. a respiratory sensor, ECG sensor, or the like. The detection unit 62 determines the contours and positions of the target volume 30 and the non-target volumes and determines parameters for the motion model based on the signal from the external sensor. The motion model predicts the target 30 and non-target volumes' positions during treatment. The planning processor 60 aligns the current target volume 30 position to the coordinate system of the radiation source assembly 32. Optionally, surgically implanted markers and/or landmarks can be used to simplify alignment. The radiation controller 64 controls the radiation source assembly 32, i.e. its rotational position, the leaves of the MLC 28, and the radiation source 24, to administer treatment at the beam trajectories and geometry according to the current radiation dose. After treatment, the dosage unit 66 uses the current beam trajectories, current beam geometry, and the determined contours and/or positions from the pre-treatment image representation and the determined motion model to determine the actual radiation dose delivered to each voxel of the target volume 30 and non-target volumes. By predicting the target 30 and non-target volumes' positions during treatment, the accuracy of the determined actual dose can be improved. The planning processor 60 updates the remaining radiation therapy plan, i.e. at least one or all of the subsequent radiation doses, according to the actual radiation delivered to the target volume 30 and non-target volumes.

Figure 5:
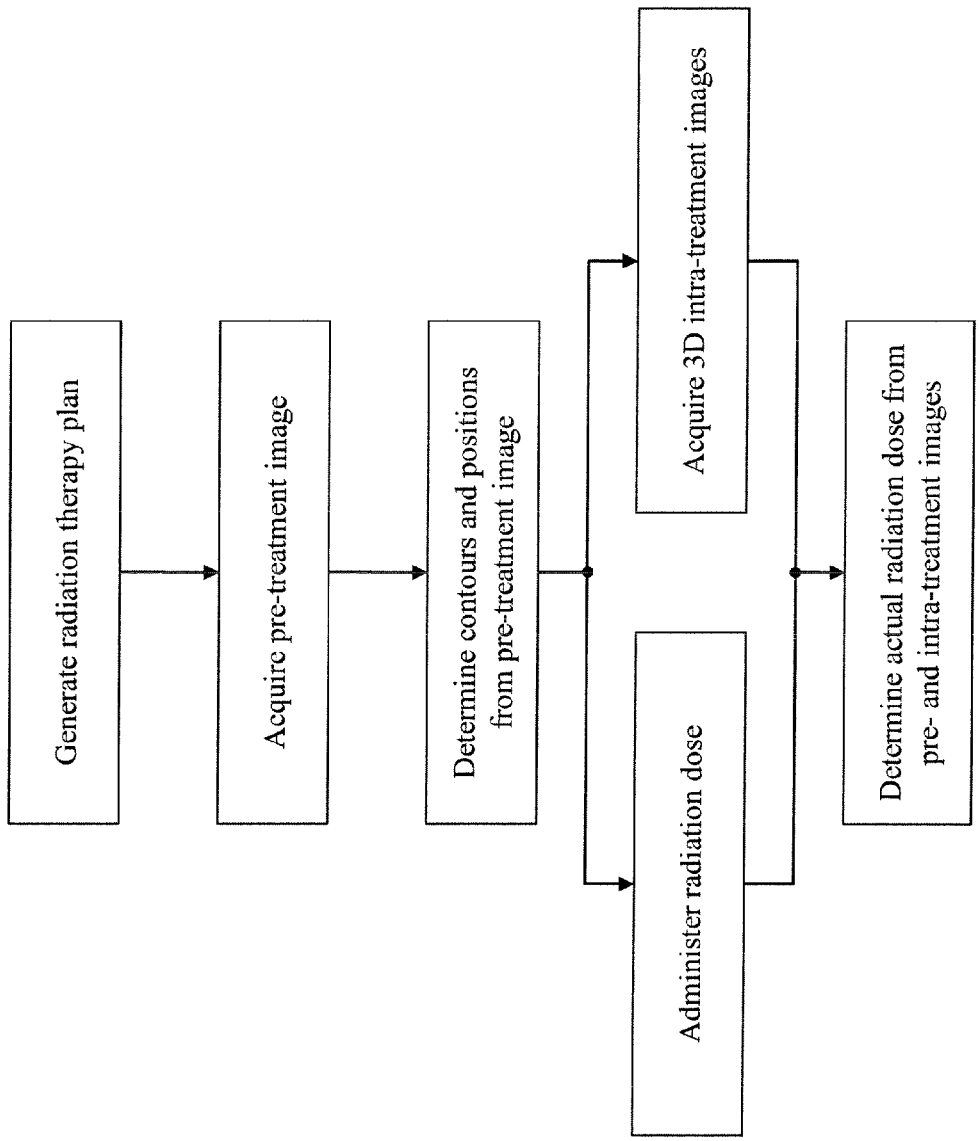
FIG. 5 is a flow chart of another method for radiation dose delivery.

With reference to FIG. 5, in a fourth aspect, after the radiation dose is delivered, the actual dose delivered to each voxel of the target 30 and non-target volumes is determined based on a pre-treatment image and a plurality of 3D intra-treatment images. Prior to administration of the radiation dose, the scanner controller 42 controls the combined MR and radiotherapy system 10 to acquire a 3D pre-treatment image representation of the target volume 30 and non-target volumes. The detection unit 62 determines the contours and positions of the target volume 30 and the non-target volumes from which the planning processor 60 aligns the current target volume 30 position to the coordinate system of the radiation source assembly 32. Optionally, surgically implanted markers and/or landmarks can be used to simplify alignment. A radiation controller 64 controls the radiation source assembly 32, i.e. its rotational position, the leaves of the MLC 28, and the radiation source 24, to administer treatment at the beam trajectories and geometry according to the current radiation dose. During the treatment, the scanner controller 42 controls the combined MR and radiotherapy system 10 to acquire a plurality of 3D intra-treatment image representations of the target volume 30 and the non-target volumes. After treatment, the detection unit 62 determines the contours and positions of the target volume 30 and the non-target volumes from the intra-treatment image representations. The dosage unit 66 uses the current beam trajectories, current beam geometry, and the determined contours and/or positions from the pre-treatment and intra-treatment image representations to determine the actual radiation dose delivered to each voxel of the target volume 30 and non-target volumes. By periodically monitoring the actual position of the target volume 30 and the non-target volumes during treatment, the accuracy of the determined actual dose can be improved. The slower time-scale of the 3D intra-treatment image representation can account for respiratory motion. The planning processor 60 updates the remaining radiation therapy plan, i.e. at least one or all of the subsequent radiation doses, according to the actual radiation delivered to the target volume 30 and non-target volumes.

Figure 6:
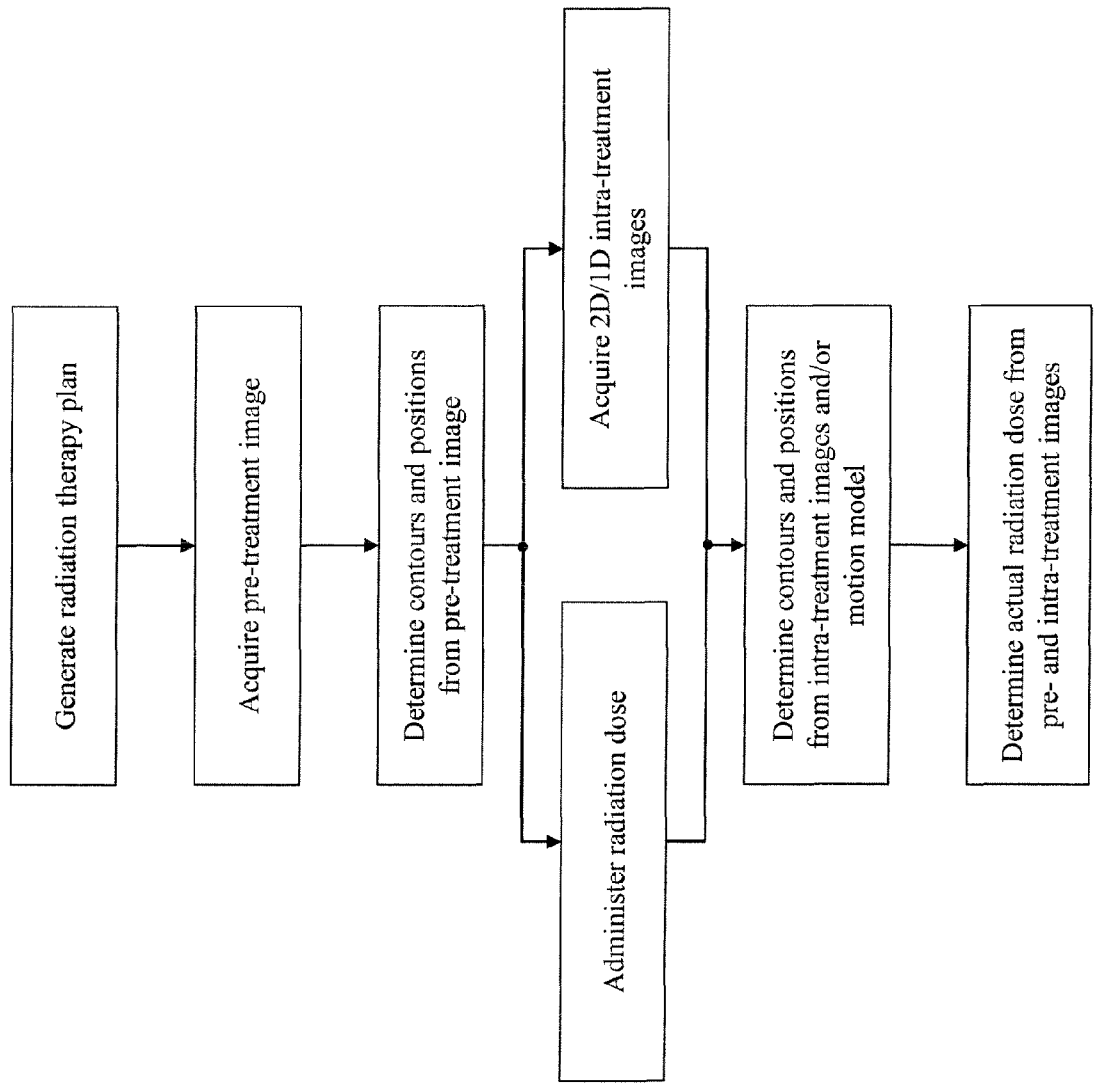
FIG. 6 is a flow chart of another method for radiation dose delivery.

With reference to FIG. 6, in a fifth aspect, after the radiation dose is delivered, the actual dose delivered to each voxel of the target 30 and non-target volumes is determined based on a pre-treatment image and a plurality of 2D/1D intra-treatment images. The shorter time interval between 2D intra-treatment images and even shorter time interval between 1D navigator pulses can account for faster pulsatile motion of the volumes. Prior to administration of the radiation dose, the scanner controller 42 controls the combined MR and radiotherapy system 10 to acquire a 3D pre-treatment image representation of the target volume 30 and non-target volumes. The detection unit 62 determines the contours and positions of the target volume 30 and the non-target volumes from which the planning processor 60 aligns the current target volume 30 position to the coordinate system of the radiation source assembly 32. Optionally, surgically implanted markers and/or landmarks can be used to simplify alignment. A radiation controller 64 controls the radiation source assembly 32, i.e. its rotational position, the leaves of the MLC 28, and the radiation source 24, to administer treatment at the beam trajectories and geometry according to the current radiation dose. During the treatment, the scanner controller 42 controls the combined MR and radiotherapy system 10 to acquire a plurality of 2D/1D intra-treatment image representations of the target volume 30 and the non-target volumes. After treatment, the detection unit 62 determines the contours and positions of the target volume 30 and the non-target volumes from the 2D/1D intra-treatment image representations. The dosage unit 66 uses the current beam trajectories, current beam geometry, and the determined contours and/or positions from the pre-treatment and intra-treatment image representations to determine the actual radiation dose delivered to each voxel of the target volume 30 and non-target volumes. By monitoring the actual position of the target volume 30 and the non-target volumes during treatment at a higher time resolution, the accuracy of the determined actual dose can be improved. The planning processor 60 updates the remaining radiation therapy plan, i.e. at least one or all of the subsequent radiation doses, according to the actual radiation delivered to the target volume 30 and non-target volumes. Alternatively, the detection unit 62 determines a motion model based on the 2D/1D intra-treatment image representations and the motion model is used to determine the actual radiation dose.

In one embodiment, the planning processor 60 updates the remaining radiation therapy plan, i.e. at least one or all of the subsequent radiation doses, automatically. In another embodiment, the radiation plan is updated under user guidance, e.g. by a physician or clinician. The physician verifies the detection of the contours and positions of the target 30 and non-target volumes on the graphic user interface 58. The high resolution image representation used in determining the therapy plan, pre-treatment image representations, intra-treatment image representations, and post-treatment image representations are displayed on the graphic user interface 58 with the contours and positions of volumes delineated. Using the input device, the physician can identify the target volume 30 and non-target volumes, i.e. sensitive tissue, organs, or the like.

In another embodiment, the planning processor 60 registers all image representations of the target 30 and non-target volumes and displays the registered image representations on the graphic user interface 58 for evaluation by a physician. Based on changes to the volumes throughout time points during the therapy plan, the physician can then choose whether to proceed with the current therapy plan, update the remaining radiation doses of the therapy plan, or cancel the therapy plan. Alternatively, the planning processor 60 displays the actual radiation dose delivered to each voxel of the target volume 30 and non-target volumes as an intensity of color map registered to one of the high resolution image representation used in determining the therapy plan, pre-treatment image representations, intra-treatment image representations, or post-treatment image representations for evaluation by the physician.

In another embodiment, a contrast-enhancing agent, e.g. gadolinium (Gd) based, super-paramagnetic iron oxide (SPIO) and ultra-small SPIO (USPIO) based, manganese (Mn) based, or the like, is introduced into the subject 22 to improve contrast of MR image representations. A contrast enhancing agent can improve contour detection and model parameter accuracy. The contrast enhancing agent is administered prior to acquiring a high-resolution, volumetric image representation for generating a radiation therapy plan and is administered prior to acquiring a pre-treatment image representation for updating the radiation therapy plan.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computer-implemented method for radiation dose delivery, the method comprising:
   generating, by a processor, a radiation therapy plan, wherein the radiation therapy plan includes a plurality of radiation doses;
   acquiring, by the processor, a pre-treatment 3D image representation of a target volume and non-target volumes;
   determining, by the processor, a contour and position of the target volume and at least one non-target volume based on the pre-treatment image representation;
   by the processor, controlling a radiation therapy apparatus to deliver the radiation dose, wherein the radiation dose includes a plurality of radiation beam trajectories and at least one radiation beam geometry;
   during administering the radiation dose, with the processor, controlling a magnetic resonance diagnostic imaging device to generate 2D intra-treatment image representations and 1D navigator pulses; and
   determining, by the processor, an actual radiation dose delivered to each region of the target volume and the at least one non-target volume based on the pre-treatment image representation, the 2D intra-treatment image representations, and the 1D navigator pulses, the radiation beam trajectories, and the at least one radiation beam geometry.

2. The method according to claim 1, further including:
   with the processor, acquiring a motion model and using the motion model in determining the actual dose delivered to each region.

3. The method according to claim 1, further including:
   during administering the radiation dose, with the processor, updating at least one remaining radiation dose of the generated radiation therapy plan based on the determined actual radiation dose.

4. The method according to claim 1, further including:
after administering the radiation dose, controlling the magnetic resonance diagnostic imaging apparatus to acquire a 3D post-treatment image representation of the target volume and the at least one non-target volume;
determining a contour and position of the target volume and at least one non-target volume based on the pre-treatment 3D image representation, the 2D intra-treatment image representations, the 1D navigator pulses, and the post-treatment 3D image representation; and
determining the actual radiation dose delivered to each region of the target volume and the at least one non-target volume based on their determined contours and positions from the pre-treatment and post-treatment 3D image representations and the 2D intra-treatment image representations, the 1D navigator pulses, the radiation beam trajectories, and the at least one radiation beam geometry.

5. The method according to claim 1, further including:
acquiring a motion signal from an external sensor during administering the radiation dose;
determining a motion model based on contours and positions of the target volume and at least one non-target volume determined from the pre-treatment 3D image representation and the acquired motion signal; and
determining the actual radiation dose delivered to each region of the target volume and the at least one non-target volume based on their determined contours and positions, the radiation beam trajectories, the at least one radiation beam geometry, the determined motion model, and the 2D image representations, the 1D navigator pulses.

6. The method according to claim 5 further including:
prior to acquiring the 3D pre-treatment image representation, surgically implanting markers.

7. The method according to claim 1, further including:
acquiring a motion signal from an external sensor during the administration of the radiation dose, acquiring a plurality of the 2D intra-treatment image representations of a target volume and non-target volumes;
acquiring a motion model; and
determining the actual radiation dose delivered to each region of the target volume and the at least one non-target volume based on their contours and positions determined from the pre-treatment image representation, the motion model, the 2D image representations, the 1D navigator pulses, the radiation beam trajectories, and the at least one radiation beam geometry.

8. The method according to claim 1, further including:
acquiring at least one of a three-dimensional (3D) intra-treatment image representation of the target volume and at least one non-target volume.

9. The method according to claim 1, wherein the step of updating the at least one remaining radiation dose is performed automatically or semi-automatically.

10. The method according to claim 1, further including:
displaying a representation of the actual radiation dose delivered to each voxel of the target volume and non-target volumes.

11. A non-transitory computer-readable medium carrying software configured to control one or more processors to perform the method according to claim 1.

12. The method according to claim 1, further including:
prior to acquiring the pre-treatment 3D image representation, introducing a contrast agent into a patient to be treated.

13. A magnetic resonance guided radiotherapy device comprising:
a magnetic resonance imaging system configured to image a subject;
a radiotherapy device configured to deliver radiation to the subject; and
one or more processors configured to perform the method according to claim 1.

14. The magnetic resonance guided radiotherapy device according to claim 13, wherein the magnetic resonance imaging system includes a split bore type magnet which defines a gap defining a radio translucent region, the radiotherapy device configured to deliver the radiation doses to the subject through the radio translucent region.

15. The method according to claim 1, wherein the magnetic resonance diagnostic imaging device includes a split bore defining a radio translucent region through which the radiation doses are delivered.

* * * * *